(12) United States Patent
Kuribayashi et al.

(10) Patent No.: US 8,431,152 B2
(45) Date of Patent: Apr. 30, 2013

(54) TRANSDERMALLY ABSORBABLE PREPARATION

(75) Inventors: Mitsuru Kuribayashi, Ibaraki (JP); Toshiro Yamaguchi, Ibaraki (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 1359 days.

(21) Appl. No.: 11/885,135

(22) PCT Filed: Feb. 28, 2006

(86) PCT No.: PCT/JP2006/303735
§ 371 (c)(1),
(2), (4) Date: Aug. 27, 2007

(87) PCT Pub. No.: WO2006/093139
PCT Pub. Date: Sep. 8, 2006

(65) Prior Publication Data
US 2009/0123526 A1 May 14, 2009

(30) Foreign Application Priority Data
Feb. 28, 2005 (JP) .................... 2005-054033

(51) Int. Cl.
*A61K 9/70* (2006.01)
*A61K 31/519* (2006.01)
(52) U.S. Cl.
USPC .................... 424/449; 424/448; 514/259.41
(58) Field of Classification Search .................... 424/448
See application file for complete search history.

(56) References Cited

U.S. PATENT DOCUMENTS

| 5,554,381 | A | 9/1996 | Roos et al. |
| 5,676,968 | A | 10/1997 | Lipp et al. |
| 5,866,157 | A | 2/1999 | Higo et al. |
| 2002/0192300 | A1* | 12/2002 | Luo et al. .................... 424/719 |
| 2004/0086552 | A1 | 5/2004 | Klokkers et al. |
| 2004/0142024 | A1 | 7/2004 | Chono et al. |
| 2005/0175676 | A1 | 8/2005 | Suzuki et al. |
| 2007/0184097 | A1* | 8/2007 | Kurita et al. .................... 424/449 |

FOREIGN PATENT DOCUMENTS

| EP | 0879051 | * 6/2003 |
| EP | 1 340 496 A1 | 9/2003 |
| EP | 1 366 762 A1 | 12/2003 |
| JP | 56-83418 | 7/1981 |
| JP | 4-59722 | 2/1992 |
| JP | 5-271056 | 10/1993 |
| JP | 6-296675 | 10/1994 |
| JP | 7-506083 | 7/1995 |

(Continued)

OTHER PUBLICATIONS

English Translation of JP 3027018.*
Third Party Observation Notice for corresponding JP Application No. JP 2007-505951. Submitted on Jan. 13, 2010.

*Primary Examiner* — Daniel Sullivan
*Assistant Examiner* — Rachael E Bredefeld
(74) *Attorney, Agent, or Firm* — Wolf, Greenfield & Sacks, P.C.

(57) ABSTRACT

A transdermally absorbable preparation that even when a drug with poor solubility in a base is added in high concentration, is stable over time and can suppress crystallization of the drug, excelling in transdermal absorbability. There is provided a transdermally absorbable preparation, comprising a base and, added thereto, at least composite particles which are composed of a silicate compound and an organic acid and a drug.

11 Claims, 1 Drawing Sheet

FOREIGN PATENT DOCUMENTS

| | | |
|---|---|---|
| JP | 8-27003 | 1/1996 |
| JP | 9-143062 A | 6/1997 |
| JP | 9-505554 | 6/1997 |
| JP | 11-302161 | 11/1999 |
| JP | 3027018 | 1/2000 |
| JP | 2004-10552 A | 1/2004 |
| JP | 2004-502725 | 1/2004 |
| JP | 3526864 | 2/2004 |
| WO | WO 99/53906 | 10/1999 |
| WO | WO 03/013611 A1 | 2/2003 |

* cited by examiner

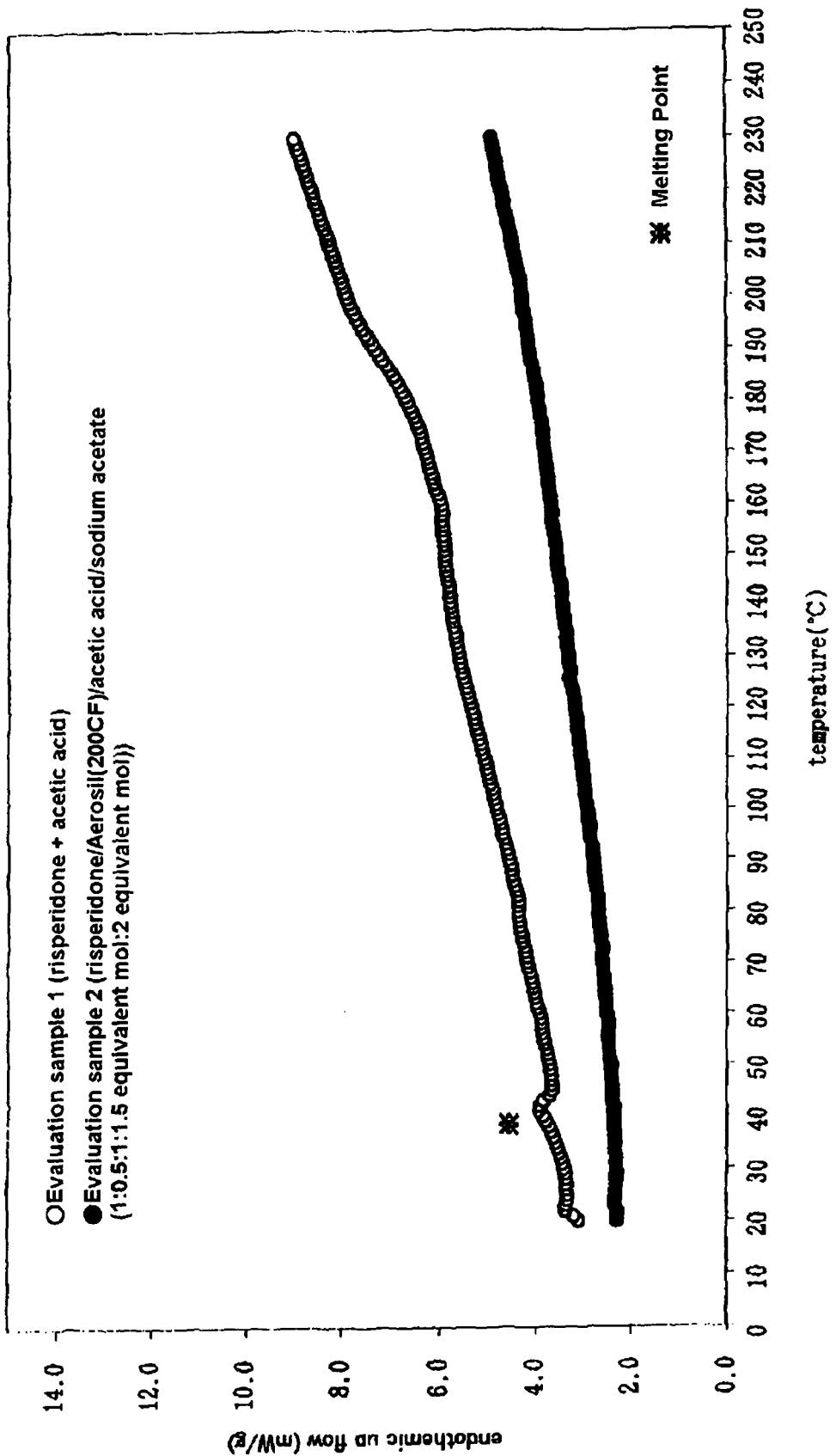

TRANSDERMALLY ABSORBABLE PREPARATION

RELATED APPLICATIONS

This application is a national stage filing under 35 U.S.C. §371 of PCT International application PCT/JP2006/303735, filed Feb. 28, 2006.

TECHNICAL FIELD

The invention relates to a transdermally absorbable preparation comprising a drug blended with a silicate compound and an organic acid.

In transdermally absorbable preparations, many attempts to improve the transdermal absorbability of an efficacious ingredient have conventionally been carried out by blending powder of a silicate compound such as silicic anhydride, an organic acid salt and the like in a base.

For example, it is reported that by making a patch blended with polyhydric alcohol, silicic anhydride and the like in a pressure-sensitive adhesive base, polyhydric alcohol is blended in more amount, and the transdermal absorbability of a drug is increased by its transdermal absorption enhancing action, and also
a pressure-sensitive adhesive property can be improved without lowering the aggregation force of a pressure-sensitive adhesive matrix by blend of silicic anhydride even blending polyhydric alcohol in much amount (ref. patent documents 1 and 2). In addition, it is reported that by making a transdermally absorbable preparation blended with powder (silicic anhydride, an organic acid salt or the like) and a drug, bioavailability of an efficacious ingredient or a release sustention can be enhanced (ref. patent document 1 and patent documents 3-6). However, the skin permeability of a drug is not sufficient even in these attempts, and therefore, a further improvement has been desired.

In the meantime, although it is necessary to blend a drug in high concentration to a pressure-sensitive adhesive base in order to improve transdermal absorbability, there was a problem that a drug low in solubility toward a base is apt to crystallize when blended in the base in high concentration. For this, it is proposed to suppress crystallization of a drug by use of silicic anhydride and the like (patent document 7).

However, because the suppression of crystallization of a drug (non-crystallization) by silicic anhydride is easily affected by temperature/humidity of a preserved atmosphere and in fact, the crystallization gradually proceeds after preparing a preparation, it is difficult to provide a preparation blended with silicic anhydride as a transdermally absorbable preparation stable over time while maintaining the transdermal absorbability of an efficacious ingredient over time, and therefore, a further pharmaceutical improvement has been required.

Consequently, the development of a transdermally absorbable preparation which is stable for an atmospheric effect and can suppress crystallization of the drug, excelling in transdermal absorbability even when a drug with poor solubility in a base is added in high concentration, has been desired. In addition, it has never been known up to now to blend composite particles which are composed of a silicate compound and an organic acid in a transdermally absorbable preparation.

Patent document 1: JP No. 3027018
Patent document 2: JP, A, 8-27003
Patent document 3: JP, A, 5-271056
Patent document 4: JP, 2004-502725 A
Patent document 5: JP, 9-505554 A
Patent document 6: JP, A, 11-302161
Patent document 7: JP No. 3526864

DISCLOSURE OF THE INVENTION

Problems to be Solved by the Invention

Consequently, the object of the invention is to provide a transdermally absorbable preparation that even when a drug with poor solubility in a base is added in high concentration, is stable over time and can suppress crystallization of the drug, excelling in transdermal absorbability.

Means for Solving Problems

During extensive research to solve the above problems, the inventors found that, by intervening an organic acid in a suppressive action for crystallization of a drug by particles of a silicate compound, crystallization of the drug is more surely suppressed, and as a result of further research, also found that, by blending composite particles of the silicate compound and the organic acid in a transdermally absorbable preparation comprising the drug and a base, an extremely excellent suppressive action of crystallization of the drug and transdermal absorbability can be achieved, and further, that a time lag till the appearance of a drug efficacy after applying the preparation to the skin can greatly be reduced; the inventors accomplished the invention.

Namely, the invention relates to a transdermally absorbable preparation, of which a base comprises composite particles, which are composed of at least a silicate compound and an organic acid, and a drug.

In addition, the invention relates to the transdermally absorbable preparation, wherein the composite particles are complexed further with a drug.

Furthermore, the invention relates to the transdermally absorbable preparation, wherein the silicate compound is silicic anhydride.

Further, the invention relates to the transdermally absorbable preparation, wherein the organic acid is one or more kinds selected from a group consisting of acetic acid, propionic acid, butyric acid, lactic acid, benzoic acid and salicylic acid.

Furthermore, the invention relates to the transdermally absorbable preparation, wherein the drug is a basic drug. In addition, the invention relates to the transdermally absorbable preparation, wherein the basic drug is risperidone or olanzapine. Furthermore, the invention relates to the transdermally absorbable preparation, wherein the base is a lipophilic base.

In addition, the invention relates to the transdermally absorbable preparation, comprising a styrene/isoprene/styrene block copolymer and/or an acrylic pressure-sensitive adhesive base as the lipophilic base.

In addition, the invention relates to the transdermally absorbable preparation, further comprising one or more kinds selected from a group consisting of propylene glycol monolaurate, isostearyl alcohol, lauric acid diethanolamide, isopropyl myristate, capric acid and sorbitan monolaurate as a transdermal absorption enhancer.

Effect of the Invention

A transdermally absorbable preparation of the invention, which comprises composite particles composed of a silicate compound, an organic acid, a drug and the like has a sufficient skin absorbability to show the drug efficacy, and since time till an permeation rate of an effective ingredient after application of the preparation becomes maximum is short, a time lag after application of the preparation is small, and therefore, the drug efficacy can be shown in a short time after application. In addition, by blending composite particles composed of a silicate compound, an organic acid, and the like, even a drug, which is poor in solubility in a base and easily crystallized conventionally, can be blended in high concentration to provide a preparation which has an excellent suppressive action of crystallization and is stable over time.

Furthermore, a transdermally absorbable preparation of the invention is high in homogeneity, favorable also in a coating aptness, and extremely excellent in a manufacturing aptness. Further, the transdermally absorbable preparation having such effects was realized for the first time in this invention by making the transdermally absorbable preparation comprising composite particles composed of a silicate compound, an organic acid, a drug, and the like.

Best Embodiment for Carrying out the Invention

As the silicate compound which can be used in the transdermally absorbable preparation of the invention, illustrative are silicic anhydride, calcium silicate, magnesium silicate, aluminum silicate, aluminum magnesium silicate, magnesium silicate aluminate, sodium magnesium silicate, and the like; among these, silicic anhydride is particularly preferable. In addition, as for silicic anhydride, although that without any treatment on the surface of minute particles (hydrophilic) and that with a lipophilic treatment on the surface are commercially available, that without any treatment (hydrophilic) is more preferable. Further, as for silicic anhydride, that with small particle diameter and large specific surface area is more preferable; for example, that in which the diameter is 7-40 nm, is commercially available and can preferably be used. Although the specific surface area of silicic anhydride is not particularly limited, it is preferably not less than 100 $m^2/g$, more preferably not less than 300 $m^2/g$.

These silicate compounds are preferably blended with 0.5-20 wt. % based on the weight of the total composition of the transdermally absorbable preparation, more preferably 2-10 wt. %, in particular preferably 3-5 wt. %. This is the reason why there is a tendency that the skin permeability is remarkably reduced over time, when the blend amount of the silicate compound is less than 0.5 wt. %, and in the meantime, when it is more than 20 wt. %, reduction of drug releasability occurs, resulting to a tendency that the skin permeability is reduced. In addition, in the invention, the silicate compound has an action to suppress separation of an absorption enhancer from a preparation (pressure-sensitive adhesive layer in case of a patch).

In the invention, although the composite particles, which are at least composed of a silicate compound and an organic acid, can be used without limitation if they are composite particles between a silicate compound and an organic acid, it is preferable that other ingredients in the transdermally absorbable preparation, in particular, a drug which is an efficacious ingredient in the preparation, and the like together form composite particles; the composite particles of the silicate compound, organic acid and drug are preferable. Namely, the above composite particles may be composed of a drug, and the like except a silicate compound, an organic acid. In the invention, the composite particles mean a composition in which a complexed ingredient is physically adsorbed on the surface of minute particles. Therefore, in the invention, the composite particles which are at least composed of a silicate compound and an organic acid mean powder particles in which at least the organic acid is physically adsorbed on surface of particles of the silicate compound; other ingredients such as a drug may physically be adsorbed to the powder particles. In the same way, in the invention, 'complexing' means physically adsorbing other ingredient (to be complexed) on the surface of minute particles; complexing of the silicate compound means physically adsorbing ingredients such as the organic acid and the drug to the silicate compound. For example, in case of forming composite particles by complexing the organic acid and the drug to the silicic anhydride, hydrophilic parts in the organic acid and the drug preferentially come close (are adsorbed) to the silanol group of silicic anhydride surface, resulting to appearance of the part of a lipophilic group in the outside; the surface of the particles apparently becomes a lipophilic state. However, the drug may not necessarily be complexed directly to particles of the silicate compound, and even without the drug is formed composite particle with the silicate compound, the transdermally absorbable preparation exerting the above excellent effect can be obtained by the invention.

In the invention, completing particles of the silicate compound with the organic acid and the like makes the surface of hydrophilic particles of the silicate compound lipophilic and improves dispersiveness in a base. Generally, the surface of particles of the silicate compound is hydrophilic, and particle dispersiveness in the base (in particular, lipophilic base) is bad, and therefore, it was difficult to make a preparation having favorable physical properties, though in the transdermally absorbable preparation of the invention, the dispersiveness in the base can be improved by making the particle surface lipophilic, whereby composite particles are formed using the organic acid and the like.

In addition, in a case that the silicate compound and the organic acid are not complexed and both are simply blended in the base (in particular, a viscous preparation such as a patch), particles of the silicate compound aggregate together, and a homogenous transdermally absorbable preparation can not be obtained. In addition, although it becomes a preparation with large variation in the transdermal absorbability, in a case that composite particles are composed of the silicate compound and the organic acid as in the preparation of the invention, not only a homogeneous preparation is obtained, but it is possible to make a preparation in which the transdermal absorbability is also homogenously favorable.

As for the organic acid forming composite particles with the silicate compound, acetic acid, fatty acid and the like can be used; among these, monovalent low molecular carboxylic acids such acetic acid, propionic acid, butyric acid, lactic acid, benzoic acid and salicylic acid are preferably used, and in particular, acetic acid is used. In addition, the organic acids may be pharmaceutically acceptable salts thereof, and may be inorganic salts or organic salts. As the above preferable salts of the organic acid, illustrative are, for example, sodium acetate and the like.

These organic acids may be used in one kind alone or in a combination of two or more kinds, and further may be used only in an acid form, or only in a salt form, or in the combination of the acid and its salt. In addition, the blend amount of the organic acid is preferably 0.5-8 mole against 1 mole of the drug, more preferably 1-6 mole, in particular preferably 2-5 mole considering stability and skin permeability as the transdermally absorbable preparation, and physical properties of the preparation. This is because when the mole ratio of the organic acid against the drug is less than 0.5, there is tendency that the transdermal absorption is reduced, and when the mole ratio exceeds 8, there is tendency that physical properties such as aggregation and dispersiveness of the base are reduced.

In the invention, complexing of micro particles (silicate compound) can be carried out, for example, by a method to mix micro particles and a complexed ingredient, a method of mixing and pulverizing, a method to coat a complexed ingredient to micro particles, and the like. Therefore, the method to form composite particles by complexing the organic acid and the like to the silicate compound is not particularly limited; however, illustrative are coating by a spray drying method and the like, mixing, mixing/pulverizing and the like, and in particular, a complexing method by mixing/grinding in a ball mill or a mortar is most preferable.

Although the drug which can be used in the transdermally absorbable preparation of the invention is not particularly limited, a basic drug can be preferably used. Examples include hypnotic/sedative agents (flurazepam hydrochloride, rilmazafone hydrochloride, etc.), antipyretic-antiinflammatory-analgesic agents (butorphanol tartarate, perisoxal citrate, etc.), excitation/analeptic agents (methamphetamine hydrochloride, methylphenidate hydrochloride, etc.), psychtropic agents (chlorpromazine hydrochloride, imipramine hydrochloride, risperidone, olanzapine, etc.), local anesthetic agents (lidocain hydrochloride, procaine hydrochloride, etc.), agents for urinary organs (oxybutynin hydrochloride, etc.), skeletal muscle relaxants (tizanidine hydrochloride, eperisone hydrochloride, pridinol mesilate, etc.), autonomic agents (carpronium chloride, neostigmine bromide, etc.), anti-Parkinson's disease agents (trihexyphenidyl hydrochloride, amantadine hydrochloride, etc.), antihistaminic agents (clemastine fumarate, diphenhydramine tannate, etc.), bronchodilator agents (tulobuterol hydrochloride, procaterol hydrochloride, etc.), cardiotonic agents (isoprenaline hydrochloride, dopamine hydrochloride, etc.), coronary dilators (diltiazem hydrochloride, verapamil hydrochloride, etc.), peripheral vasodilators (nicametate citrate, tolazoline hydrochloride, etc.), agents for circulatory organs (flunarizine hydrochloride, nicardipine hydrochloride, etc.), antiarrhythmic agents (propranolol hydrochloride, alprenolol hydrochloride, etc.), antiallergic agents (ketotifen fumarate, azelastine hydrochloride, etc.), anti-dizziness agents (betahistine mesilate, difenidol hydrochloride, etc.), serotonin receptor antagonistic agents, narcotic analgesic agents (morphine sulfate, fentanyl citrate, etc.). Among these, in particular, risperidone or olanzapine are preferable. In addition, the invention is also effective toward a basic drug which is easily crystallized in a base.

Such a drug may be used in the free basic form, in its pharmaceutically acceptable acid addition salt form, or in combination of these. Further, the above drugs may be used in one kind alone or in a combination of two or more kinds. These drugs is blended preferably in 3-30 wt. % based on the weight of the total composition of the transdermally absorbable preparation in view of physical properties of the preparation and the transdermal absorbability, more preferably in 5-20 wt. %, in particular preferably in 10-20 wt. %.

Although in the transdermally absorbable preparation of the invention, a base according to its dosage form can be blended except the above ingredients, it is preferable that the base used in the transdermally absorbable preparation of the invention is a lipophilic base. It is because the organic acid, the drug and the like, which form composite particles, are separated from the silicate compound when using hydrophilic base, and the suppression action for crystallization is reduced.

As the lipophilic base which can be used in the invention, examples include preferably Vaseline®, carnauba wax, candelilla wax, beeswax, plastibase, microcrystalline wax, lanolin, liquid paraffin, styrene/isoprene/styrene block copolymer, acrylic pressure-sensitive adhesive base, polyisobutylene, and polydimethylsiloxane. These may be used in one kind alone, or in a combination of two or more kinds.

Although the acrylic pressure-sensitive adhesive base can be used without limitation, as long as it is alkyl acrylate ester copolymer consisting of polymer which makes alkyl acrylate ester or alkyl methacrylate ester as a main monomer, the carbon number of an alkyl group is preferably 4-16. In addition, although the main monomer may be copolymerized with a monomer such as acrylic acid, methacrylic acid, hydroxyalkyl acrylate ester, hydroxyalkyl methacrylate ester, vinyl acetate, or vinylpyrrolidone, a copolymerization ratio of the main monomer is preferably at least 50% in view of pressure-sensitive adhesive characteristics of the base.

The blend amount of these bases is not particularly limited and can appropriately be adjusted according to blend amount of the other ingredients except the bases; however, these bases are blended preferably in 50-95 wt. % based on the weight of the total composition of the transdermally absorbable preparation in consideration of the blend amount of other ingredients contained in the preparation, more preferably in 60-90 wt. %.

In addition, as a dosage form of the transdermally absorbable preparation of the invention illustrative are an ointment, a patch, or the like. For example, in a case that the dosage form is a patch, among the above lipophilic bases, styrene/isoprene/styrene block copolymer and acrylic pressure-sensitive adhesive base are used in particular preferably as a pressure-sensitive adhesive base; however, it is also preferable that two or more of the above lipophilic bases are used in combination, being blended with styrene/isoprene/styrene block copolymer and acrylic pressure-sensitive adhesive base. Further, except the above base, an acrylic pressure-sensitive adhesive agent (non-functionality) and the like may be blended, and furthermore, a tackifying resin may be added according to adhesiveness. As usable tackifying resins, illustrative are rosin derivatives (e.g., rosin, glycerin esters of rosin, hydrogenated rosin, glycerin esters of hydrogenated rosin, pentaerythritol esters of rosin and the like), alicyclic saturated hydrocarbon resins (e.g., Arkon P 100, Arakawa Chemical Industries, Co., Ltd.), aliphatic hydrocarbon resins (e.g., Quintone B 170, Zeon Corporation), terpene resins (e.g., Clearon P-125, Yasuhara Chemical), maleic acid resins and the like. Among these tackifying resins, in particular, glycerin esters of hydrogenated rosin, alicyclic saturated hydrocarbon resins, aliphatic hydrocarbon resins and terpene resins are preferable. These tackifying resins may be used in one kind alone or two or more kinds in combination.

Further, a plasticizer may be blended in the above pressure-sensitive adhesive base. As plasticizers which can be used in the invention, illustrative are petroleum oils (e.g., paraffin type process oil, and the like), squalane, squalene, vegetable oils (e.g., olive oil, camellia oil, castor oil, tall oil, peanut oil), dibasic acid esters (e.g., adipate esters and the like), liquefied rubber (e.g., polybutene, liquefied isoprene rubber), diethylene glycol, polyethylene glycol, glycol salicylate, propylene glycol, dipropylene glycol, crotamiton and the like. Among these, in particular, liquid paraffin, liquefied polybutene, glycol salicylate, and crotamiton are preferable.

In addition, in a case that the dosage form is an ointment, a non-aqueous base such as Vaseline is used, and except to the above plasticizers, a higher fatty acid such as myristic acid, or its ester, waxes such as whale wax, a surfactant or the like are preferably blended. As surfactants used, a non-ionic surfactant is preferable; illustrative are, for example, glycerin monostearate, glycerin monooleate, cetomacrogol and the like.

In the transdermally absorbable preparation of the invention, an absorption enhancer may further be blended appropriately. As the absorption enhancer used in the invention, illustrative are fatty alcohols such as isostearyl alcohol, fatty acids such as capric acid, fatty acid derivatives such as propylene glycol monolaurate, isopropyl myristate and sorbitan monolaurate, propylene glycol, polyethylene glycol, lauric acid diethanolamide, and the like; among these, propylene glycol monolaurate, isostearyl alcohol, lauric acid diethanolamide, isopropyl myristate, capric acid, and sorbitan monolaurate are preferably used. These absorption enhancers may be used in one kind alone or in combination of two or more kinds. In addition, the blend amount of the absorption enhancer is preferably 1-10 wt. %, more preferably 2-8 wt. % and in particular preferably 3-6 wt. %, by consideration on sufficient permeability of an efficacious ingredient to the skin as a preparation, skin irritation and the like.

In addition, if necessary, other agents such as an antioxidant, filler, cross-linking agent, preservative, ultraviolet absorber and resolvent may be blended in the transdermally absorbable preparation of the invention.

The transdermally absorbable preparation of the invention can be prepared by one of any known method. For example, after a silicate compound, an organic acid and a drug are simultaneously mixed/pulverized, or after mixing/pulverizing the silicate compound and the organic acid, the drug is mixed/pulverized, or after mixing/pulverizing the silicate compound and the drug, the organic acid is mixed/pulverized, and a mixture is dissolved in solvents such as methylene chloride, toluene, hexane or ethyl acetate together with a pressure-sensitive adhesive base ingredient, coated on a releasable liner or a backing, and the solvent is removed by drying, then the resultant is attached to the backing or the releasable liner to obtain the preparation.

The ointment by the invention can be prepared by one of any known method. For example, after a silicate compound, an organic acid and a drug are simultaneously mixed/pulverized, or after mixing/pulverizing the silicate compound and the organic acid, the drug is mixed/pulverized, or after mixing/pulverizing the silicate compound and the drug, the organic acid is mixed/pulverized, and a mixture is added with a substance in which a higher fatty acid ester, wax, surfactant or hydrocarbon are separately heated or heated/dissolved, and homogeneously mixed by a puddle-mixer, followed by being cooled to room temperature under stirring to obtain an ointment.

In the following, the invention is explained in more detail by test examples and examples, and however, a dosage form and a formula are not limited to these examples. In addition, various modifications may be possible without departing from the technical idea of the invention.

Differential Scanning Calorimetric Test

In a differential scanning calorimeter DSC-7 (manufactured by Perkin-Elmer Co., Ltd.), an evaluation sample 5-20 mg and as a reference, a silicate compound corresponding to the evaluation sample are set in a cell (made by aluminum), and warmed from about 20° C. to about 230° C. at the rate of 5° C./min to detect and record an endothermic-exothermic calorie difference. The results are shown in FIG. 1.

As the evaluation samples, the evaluation sample 1, in which risperidone and acetic acid (1 mole against risperidone 1 mole) were simply mixed, and the evaluation sample 2 were used, in which risperidone was added with silicic anhydride (Aerosil® 200CF) (0.5 weight part against risperidone 1 weight part), acetic acid (1.5 mole against risperidone 1 mole) and sodium acetate (2 mole against risperidone 1 mole), and pulverized by a powdering machine.

As shown in FIG. 1, in the evaluation sample 1 in which risperidone and acetic acid were simply mixed, the melting point was observed around 40° C., whereas in the evaluation sample 2 in which the silicate compound, acetic acid and risperidone formed composite particles, the melting point was not observed, and thus, the drug was let be non-crystallized by formation of composite particles of the silicate compound.

EXAMPLE

Preparation Example: Preparation of Transdermally Absorbable Preparation (Example 1-20 and Comparative Example 1-8)

Each preparation was prepared by the following procedure according to each formula described in the below Table 1-Table 3.

Examples 1-17

(1) Acetic acid, sodium acetate and risperidone were added to a silicate compound and pulverized by a powder machine.

(2) (1) and other ingredients in Table 1 or Table 2 (pressure-sensitive adhesive bases and transdermal absorption enhancers) were dissolved in toluene (solid proportion, about 60%), a solution was extended on the silicone treatment surface of polyethylene terephthalate film (releasable liner, 75 μm), and dried at 70° C. for 10 minutes. Then, polyethylene terephthalate film (sand-matte, 25 μm) was laminated to obtain a patch of the transdermal absorbable preparation of the invention (the examples 1-17). The thickness of the pressure-sensitive adhesive layer was about 80 μm in each.

Examples 18-20

(1) Acetic acid, sodium acetate and olanzapine were added to a silicate compound and pulverized by a powder machine.

(2) (1) and other ingredients in Table 3 (pressure-sensitive adhesive bases and transdermal absorption enhancers) were dissolved in toluene (in the examples 18 and 19, the solid content is about 60%; in the example 20, the solid portion is about 45%), a solution was coated on the silicone treatment surface of polyethylene terephthalate film (releasable liner, 75 μm), and dried at 70° C. for 10 minutes. Then, polyethylene terephthalate film (sand-matte, 25 μm) was laminated to obtain a patch of the transdermal absorbable preparation of the invention (the examples 18-20). The thickness of the pressure-sensitive adhesive layer was about 80 μm in each.

Here, the silicate compounds used in each example were respectively as follows.

Examples 1-3 and 17-20: Silicic anhydride (Aerosil 200CF), particle diameter 12 nm, specific surface area: 200 m$^2$/g, hydrophilic Example 4: Silicic anhydride (Aerosil 50), particle diameter 30 nm, specific surface area: 50 m$^2$/g, hydrophilic Examples 5 and 12-16: Silicic anhydride (Aerosil 300CF), particle diameter 7 nm, specific surface area: 300 m$^2$/g, hydrophilic Example 6: Silicic anhydride (Aerosil 380), particle diameter 7 nm, specific surface area: 380 m$^2$/g, hydrophilic Example 7: Silicic anhydride (Aerosil R972), particle diameter 16 nm, hydrophobic Example 8: Silicic anhydride (Aerosil 812), particle diameter 7 nm, hydrophobic Example 9: Silicic anhydride (Aerosil R812S), particle diameter 7 nm, hydrophobic Examples 10 and 11: Calcium silicate (FLORITE®-RE).

Comparative Example 1

(1) Risperidone was added to the silicate compound (Aerosil 200CF) and pulverized by a powder machine.

(2) (1) and other ingredients in Table 1 (pressure-sensitive adhesive bases) were dissolved in toluene (solid content, about 60%), a solution was extended on the silicone treatment surface of polyethylene terephthalate film (releasable liner, 75 μm), and dried at 70° C. for 10 minutes. Then, polyethylene terephthalate film (sand-matte, 25 μm) was laminated to obtain a patch which is a transdermal absorbable preparation in the comparative example (the comparative example 1). The thickness of the pressure-sensitive adhesive layer was about 80 μm.

Comparative Examples 2-8

All the ingredients of Table 1 or Table 2 were dissolved in toluene (solid content, about 60%), a solution was extended on the silicone treatment surface of polyethylene terephthalate film (relesable liner, 75 μm), and dried at 70° C. for 10 minutes. Then, polyethylene terephthalate film (sand-matte, 25 μm) was laminated to obtain a patch which is a transdermal absorbable preparation of the comparative example (the comparative examples 2-8). The thickness of the pressure-sensitive adhesive layer was about 80 μm in each.

Here, as to the silicate compound, silicic anhydride (Aerosil 200CF) was used in the comparative example 5.

TABLE 1

| Examples No. | Pressure-sensitive adhesive base SIS/Arkon P-100/Liquid paraffin (Composition weight ratio) | % | Drug Risperidone % | Orginic acid Acetic acid % | Mole ratio | Sodium acetate % | Mole ratio | Silicate compound | % |
|---|---|---|---|---|---|---|---|---|---|
| Example 1 | (10/30/15) | 73.6 | 10 | 4.4 | 3 | 4.0 | 2 | SiO2(Aerosil 200CF) | 5 |
| Example 2 | (10/30/15) | 70.6 | 10 | 4.4 | 3 | 4.0 | 2 | SiO2(Aerosil 200CF) | 5 |
| Example 3 | (10/30/15) | 67.6 | 10 | 4.4 | 3 | 4.0 | 2 | SiO2(Aerosil 200CF) | 5 |
| Example 4 | (10/30/15) | 70.6 | 10 | 4.4 | 3 | 4.0 | 2 | SiO2(Aerosil 50) | 5 |
| Example 5 | (10/30/15) | 70.6 | 10 | 4.4 | 3 | 4.0 | 2 | SiO2(Aerosil 300CF) | 5 |
| Example 6 | (10/30/15) | 70.6 | 10 | 4.4 | 3 | 4.0 | 2 | SiO2(Aerosil 380) | 5 |
| Example 7 | (10/30/15) | 70.6 | 10 | 4.4 | 3 | 4.0 | 2 | SiO2(Aerosil R972) | 5 |
| Example 8 | (10/30/15) | 70.6 | 10 | 4.4 | 3 | 4.0 | 2 | SiO2(Aerosil R812) | 5 |
| Example 9 | (10/30/15) | 70.6 | 10 | 4.4 | 3 | 4.0 | 2 | SiO2(Aerosil R812S) | 5 |
| Example 10 | (10/30/15) | 72.6 | 10 | 4.4 | 3 | 4.0 | 2 | Ca Silicate(Florite-RE) | 3 |
| Example 11 | (10/30/15) | 70.6 | 10 | 4.4 | 3 | 4.0 | 2 | Ca Silicate(Florite-RE) | 5 |
| Comparative example 1 | (10/30/15) | 85.0 | 10 | — | — | — | — | SiO2(Aerosil 200CF) | 5 |
| Comparative example 2 | (10/30/10) | 81.6 | 10 | 4.4 | 3 | 4.0 | 2 | — | |
| Comparative example 3 | (10/30/10) | 78.6 | 10 | 4.4 | 3 | 4.0 | 2 | — | |
| Comparative example 4 | (10/30/15) | 75.6 | 10 | 4.4 | 3 | 4.0 | 2 | — | |
| Comparative example 5 | (10/30/15) | 73.6 | 10 | 4.4 | 3 | 4.0 | 2 | SiO2(Aerosil 200CF) | 5 |

| Examples No. | Transdermal absorbtion enhancer PGML % | ISA % | Skin permeability Maximum skin permeation rate (μg/cm2/hr) | Tmax (hr) | Physical properties |
|---|---|---|---|---|---|
| Example 1 | 3 | — | 33.20 | 9 | ○ |
| Example 2 | 6 | — | 39.30 | 7 | ○ |
| Example 3 | 6 | 3 | 49.47 | 9 | ○ |
| Example 4 | 6 | — | 37.40 | 9 | ○ |
| Example 5 | 6 | — | 39.15 | 9 | ○ |
| Example 6 | 6 | — | 41.81 | 7 | ○ |
| Example 7 | 6 | — | 38.25 | 9 | ○ |
| Example 8 | 6 | — | 35.63 | 9 | ○ |
| Example 9 | 6 | — | 35.62 | 9 | ○ |
| Example 10 | 6 | — | 33.22 | 9 | ○ |
| Example 11 | 6 | — | 33.34 | 9 | ○ |
| Comparative example 1 | — | — | 0.75 | >23 | ○ |
| Comparative example 2 | — | — | 11.63 | >23 | ○ |
| Comparative example 3 | 3 | — | 61.51 | 15 | ○ |
| Comparative example 4 | 6 | — | 40.46 | 7 | x |
| Comparative example 5 | 3 | — | 34.87 | 7 | x |

% in Table 1 entirely means weight %.
All mole ratio in Table 1 mean the mole ratio against the drug (risperidone).
SIS: (Kraton polymer) styrene/isoprene/styrene block copolymer Arkon p-100: Tackifying resin (Arakawa Chemical Industries Co., Ltd.)
PGML: Propylene glycol monolaurate
ISA: Isostearyl alcohol

TABLE 2

| Examples No. | Pressure-sensitive adhesive base SIS/Arkon P-100/ Liquid paraffin (Composition weight ratio) | % | Acrylic pressure-sensitive adhesive base % | Drug Risperidone % | Organic acid Acetic acid % | Mole ratio | Sodium acetate % | Mole ratio | Silicate compound | % |
|---|---|---|---|---|---|---|---|---|---|---|
| Example 12 | (10/35/10) | 58.6 | *10 | 10 | 4.4 | 3 | 4 | 2 | SiO2(Aerosil 300CF) | 5 |
| Example 13 | (10/35/10) | 62.26 | *10 | 8 | 3.54 | 3 | 3.2 | 2 | SiO2(Aerosil 300CF) | 5 |
| Example 14 | (10/35/10) | 65.95 | *10 | 6 | 2.65 | 3 | 2.4 | 2 | SiO2(Aerosil 300CF) | 5 |
| Example 15 | (10/35/10) | 53.65 | *15 | 10 | 4.4 | 3 | 4 | 2 | SiO2(Aerosil 300CF) | 5 |
| Example 16 | (10/35/10) | 54.6 | *15 | 10 | 4.4 | 3 | 4 | 2 | SiO2(Aerosil 300CF) | 5 |
| Example 17 | (10/35/10) | 55.6 | **15 | 10 | 4.4 | 3 | 4 | 2 | SiO2(Aerosil 200CF) | 3 |
| Comparative example 6 | (10/35/10) | 58.65 | *15 | 10 | 4.4 | 3 | 4 | 2 | — | |
| Comparative example 7 | (10/35/10) | 58.6 | *15 | 10 | 4.4 | 3 | 4 | 2 | — | |
| Comparative example 8 | (10/35/10) | 58.6 | **15 | 10 | 4.4 | 3 | 4 | 2 | — | |

| Examples No. | Transdermal absorbtion enhancer PGML % | SML % | CA % | Skin permeability Maximum skin permeation rate (μg/cm2/hr) | Tmax (hr) | Physical properties |
|---|---|---|---|---|---|---|
| Example 12 | 7 | — | 1 | 73.24 | 9 | ○ |
| Example 13 | 7 | — | 1 | 52.55 | 7 | ○ |
| Example 14 | 7 | — | 1 | 40.65 | 9 | ○ |
| Example 15 | 7 | — | 0.95 | 70.90 | 11 | ○ |
| Example 16 | 7 | — | — | 66.48 | 11 | ○ |
| Example 17 | 7 | 1 | — | 56.80 | 9 | ○ |
| Comparative example 6 | 7 | — | 0.95 | 55.71 | 7 | x |
| Comparative example 7 | 7 | 1 | — | 48.11 | 9 | x |
| Comparative example 8 | 7 | 1 | — | 40.44 | 11 | x |

% in Table 2 entirely means weight %.
All mole ratio in Table 2 mean the mole ratio against the drug (risperidone).
SIS: (Kraton polymer) styrene/isoprene/styrene block copolymer
Arkon p-100: Tackifying resin (Arakawa Chemical Industries Co., Ltd.)
PGML: Propylene glycol monolaurate
SML: Sorbitan monolaurate
CA: Capric acid
*Self cross-linking copolymer between acrylate and vinyl acetate, solid portion 41.5%
**Self cross-linking copolymer between acrylate and vinyl acetate, solid portion 45%
¢ It means wt. % as a solid proportion.

TABLE 3

| Examples No. | pressure-sensitive adhesive base SIS/Arkon P-100/ Liquid paraffin (Composition weight ratio) | % | Acrylic pressure-sensitive adhesive base % | Drug Olanzapine % | Organic acid Acetic acid % | Mole ratio | Sodium acetate % | Mole ratio | Silicate compound | % | Transdermal absorbtion enhancer PGML % |
|---|---|---|---|---|---|---|---|---|---|---|---|
| Example 18 | (10/35/10) | 67.96 | — | 10 | 5.8 | 3 | 5.24 | 2 | SiO2(Aerosil 200CF) | 5 | 6 |
| Example 19 | (10/35/10) | 57.96 | 10 | 10 | 5.8 | 3 | 5.24 | 2 | SiO2(Aerosil 200CF) | 5 | 6 |
| Example 20 | — | | 69.2 | 10 | 5.8 | 3 | 4 | 1.5 | SiO2(Aerosil 200CF) | 5 | 6 |

% in Table 3 entirely means weight %.
Mole ratio in Table 3 entirely means the mole ratio against the drug (olanzapine).
SIS: (Kraton polymer) styrene/isoprene/styrene block copolymer
Arkon p-100: Tackifying resin (Arakawa Chemical Industries Co., Ltd.)
PGML: Propylene glycol monolaurate
*Self cross-linking copolymer between acrylate and vinyl acetate, solid portion 41.5%
¢ It means wt. % as a solid proportion.

Test Example 1

In Vitro Skin Permeability Test

An abdominal part skin of a hairless mouse was excised, and then, the dermal side was placed to a receptor side and installed in a flow-through Franz type cell (3.14 cm2) in which warm water of 32° C. was circulated around the outer part. The transdermally absorbable preparations of the invention (the examples 1-17) prepared as described above or the transdermally absorbable preparations of the comparative example (the comparative examples 1-8) were applied to the stratum corneum layer side, and samplings were carried out at every two hours for 24 hours at a rate of 5.5 ml/hr. As for the receptor layer, saline was used. The content of risperidone in a receptor liquid at each hour was measured by a high-performance liquid chromatography method; the maximum skin permeation rate per hour (μg/cm²/hr) of risperodone for each preparation and the time ($T_{max}$) reaching to the maximum skin permeation rate were calculated to show the results in Table 1 and Table 2.

As is evident from the results in Table 1 and table 2, all of the transdermally absorbable preparations of the invention (the examples 1-17) exceed 30 µg/cm²/hr in the maximum skin permeation rate, and are tremendously improved in the skin permeability compared with conventional preparations (the comparative examples 1 and 2) to show that they have sufficient skin permeability to exert the drug efficacy. In addition, as for the preparations of the invention, all the Tmax are 7-11 hours, and therefore, it is possible to exert the drug efficacy at short times after application of the preparations, and it became evident that the time lag till appearance of the drug efficacy after application of the preparations to the skin is greatly shortened compared with that of conventional preparations (the comparative examples 1-3).

Test Example 2

Evaluation on Physical Properties of Preparation

As for the transdermally absorbable preparations of the invention (the examples 1-17) and the transdermally absorbable preparations of the comparative example (the comparative examples 1-8) prepared as described above, the characteristics of each preparation were observed on fluidity, homogeneity, dispersiveness and the like, and evaluated collectively as either O (favorable) or X (poor) as a manufacturing aptness. The results are shown in Table 1 a d Table 2.

As shown in the results of Table 1 and Table 2, all of the transdermally absorbable preparations of the invention (the examples 1-17), in which composite particles are composed of an organic acid and a silicate compound, are excellent in physical properties. All of these preparations are excellent in dispersiveness and fluidity of an adhesive mass, further high in homogeneity and extremely favorable in a coating aptness. On the contrary, as to the comparative example 4, the absorption enhancer (PGML) bled to the surface of the pressure-sensitive adhesive agent, and the physical properties were bad. Further, although in the comparative example 5, the organic acid and the silicate compound were contained as constituting ingredients of the preparation, it was the preparation in which these did not form composite particles and became a highly viscous adhesive mass, whereby a coating liquid was too high in thixotropy to coat it homogeneously. All the comparative examples 6-8 were lack in an aggregation force; when releasing after applying the preparations to the skin, a residue remained to show poor physical properties. In addition, the comparative example 8 was poor in compatibility of the base to produce separation when coating an adhesive mass.

Therefore, by the above results, the transdermally absorbable preparation of the invention, which comprised composite particles composed of a silicate compound, an organic acid, a drug and the like, was one wherein a blended drug was non-crystallized and also had a sufficient skin permeability to show the drug efficacy, and a time lag till appearance of the drug efficacy after applying the preparation was small, and therefore, it was shown that it was excellent for exerting the drug efficacy. Furthermore, it was shown that the transdermally absorbable preparation of the invention was excellent in the fluidity and dispersiveness of an adhesive mass, high in homogeneity, favorable in a coating aptness and extremely excellent in a manufacturing aptness.

INDUSTRIAL APPLICABILITY

As explained above, according to the invention, it becomes possible to provide a transdermally absorbable preparation with extremely favorable transdermal absorbability of a drug in a preparation, small in a time lag till appearance of the drug efficacy after application to the skin, and excellent in physical properties; therefore, the transdermally absorbable preparation is expected as a pharmaceutical agent such as an ointment or a patch.

BRIEF DESCRIPTION OF THE DRAWINGS

FIG. 1 is the drawing indicating non-crystallization of the drug.

The invention claimed is:

1. A transdermally absorbable preparation comprising a base, wherein the base comprises composite particles composed of micro particles of a silicate compound and one or more ingredient(s), wherein the one or more ingredients comprises at least one or more drug(s) and one or more organic acid(s) and/or one or more pharmaceutically acceptable salt(s) thereof, wherein the one or more drug(s) is/are a risperidone and/or an olanzapine and the one or more organic acid(s) is/are selected from a group consisting of acetic acid, propionic acid, a butyric acid, a lactic acid, a benzoic acid, and a salicylic acid, and wherein the one or more ingredient(s) is/are physically adsorbed on the surface of the micro particles of the silicate compound.

2. The transdermally absorbable preparation according to claim 1, wherein the silicate compound is a silicic anhydride.

3. The transdermally absorbable preparation according to claim 1, wherein the base is a lipophilic base.

4. The transdermally absorbable preparation according to claim 3, comprising a styrene/isoprene/styrene block copolymer and/or an acrylic pressure-sensitive adhesive base as the lipophilic base.

5. The transdermally absorbable preparation according to claim 1 further comprising one or more kinds selected from a group consisting of a propylene glycol monolaurate, an isostearyl alcohol, a lauric acid diethanolamide, an isopropyl myristate, a capric acid and a sorbitan monolaurate as a transdermal absorption enhancer.

6. The transdermally absorbable preparation according to claim 2, wherein the one or more drug(s) is a risperidone and the one or more organic acid(s) is an acetic acid.

7. The transdermally absorbable preparation according to claim 6, comprising styrene/isoprene/styrene block copolymer and/or an acrylic pressure-sensitive adhesive base as a lipophilic base.

8. The transdermally absorbable preparation according to claim 7, further comprising one or more kinds selected from a group consisting of a propylene glycol monolaurate, an isostearyl alcohol, a lauric acid diethanolamide, an isopropyl myristate, a capric acid and a sorbitan monolaurate as a transdermal absorption enhancer.

9. The transdermally absorbable preparation according to claim 7, wherein the lipophilic base is styrene/isoprene/styrene block copolymer.

10. The transdermally absorbable preparation according to claim 9, further comprising one or more kinds selected from a group consisting of a propylene glycol monolaurate, an isostearyl alcohol, a lauric acid diethanolamide, an isopropyl myristate, a capric acid and a sorbitan monolaurate as a transdermal absorption enhancer.

11. A transdermally absorbable preparation comprising a base and one or more drug(s), wherein the base comprises composite particles composed of micro particles of a silicate compound and one or more ingredient(s), wherein the one or more ingredients comprises at least one or more organic acid(s) and/or one or more pharmaceutically acceptable salt(s) thereof, wherein the one or more drug(s) is/are a risperidone and/or an olanzapine and the one or more organic acid(s) is/are selected from a group consisting of acetic acid, propionic acid, a butyric acid, a lactic acid, a benzoic acid, and a salicylic acid, and wherein the one or more ingredient(s) is/are physically adsorbed on the surface of the micro particles of the silicate compound.

\